(12) United States Patent
Callahan

(10) Patent No.: US 10,330,603 B1
(45) Date of Patent: *Jun. 25, 2019

(54) MASS PRODUCED, LOW COST, PORTABLE TEST KIT FOR THE DETECTION AND IDENTIFICATION OF CHEMICAL AND BIOLOGICAL AGENTS

(71) Applicant: Michael D. Callahan, Englewood, CO (US)

(72) Inventor: Michael D. Callahan, Englewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/670,227

(22) Filed: Aug. 7, 2017

Related U.S. Application Data

(63) Continuation-in-part of application No. 15/094,825, filed on Apr. 8, 2016, now Pat. No. 9,759,733.

(51) Int. Cl.
*G01N 21/78* (2006.01)
*G01N 33/94* (2006.01)
*G01N 21/77* (2006.01)

(52) U.S. Cl.
CPC ..... *G01N 21/78* (2013.01); *G01N 2021/7759* (2013.01)

(58) Field of Classification Search
CPC ............................... G01N 21/78; G01N 33/94
USPC .......... 422/400, 411, 418, 425, 430; 436/92, 436/164
See application file for complete search history.

(56) References Cited

U.S. PATENT DOCUMENTS

| | | | | |
|---|---|---|---|---|
| 3,329,486 A | * | 7/1967 | Rupe ..................... | G01N 33/52 422/420 |
| 3,616,251 A | * | 10/1971 | Linoli ..................... | C12Q 1/00 422/404 |
| 3,713,779 A | | 1/1973 | Sirago et al. | |
| 3,748,098 A | * | 7/1973 | Dutch ..................... | B01L 3/505 206/471 |
| 3,770,383 A | * | 11/1973 | Price ................. | G01N 33/54313 422/425 |
| 3,915,639 A | * | 10/1975 | Friedenberg ........... | G01N 31/22 422/401 |
| 3,954,412 A | * | 5/1976 | Ogawa ................... | G01N 33/64 422/420 |
| 3,955,926 A | * | 5/1976 | Fischer .................. | G01N 31/22 436/92 |
| 3,972,992 A | * | 8/1976 | Cleeland, Jr. ........... | C08C 19/36 436/533 |

(Continued)

FOREIGN PATENT DOCUMENTS

AU 2003100271 7/2003
AU 2005100056 5/2005
(Continued)

OTHER PUBLICATIONS

Alliston, G. V. et al, Analyst 1972, 97, 263-265.*
(Continued)

*Primary Examiner* — Arlen Soderquist
(74) *Attorney, Agent, or Firm* — Shifrin Patent Law; Dan Shifrin

(57) ABSTRACT

A highly portable, paper and swab-based detection kit is provided for identifying chemical and biological agents. A method of mass manufacture providing low cost kits with long term commercial shelf life and a method of use is also provided.

32 Claims, 1 Drawing Sheet

(56) References Cited

U.S. PATENT DOCUMENTS

| | | | | |
|---|---|---|---|---|
| 4,110,078 A * | 8/1978 | Zelonis | G01N 33/946 | 436/92 |
| 4,196,167 A * | 4/1980 | Olsen | G01N 31/22 | 422/411 |
| 4,288,344 A * | 9/1981 | Reiss | G01N 31/22 | 436/901 |
| 4,320,086 A * | 3/1982 | Reiss | G01N 33/946 | 422/420 |
| 4,752,448 A * | 6/1988 | Wells | G01N 33/946 | 422/420 |
| 4,771,005 A * | 9/1988 | Spiro | C09B 67/0079 | 422/400 |
| 4,786,595 A * | 11/1988 | Arai | C12Q 1/26 | 422/421 |
| 4,788,039 A * | 11/1988 | Glattstein | G01N 31/22 | 252/193 |
| 4,806,487 A * | 2/1989 | Akers | G01N 33/94 | 436/169 |
| 4,812,413 A * | 3/1989 | Glattstein | G01N 33/946 | 422/413 |
| 4,816,415 A * | 3/1989 | Akers | G01N 33/948 | 436/169 |
| 4,840,912 A * | 6/1989 | Glattstein | G01N 33/946 | 436/901 |
| 4,877,580 A * | 10/1989 | Aronowitz | G01N 21/78 | 422/401 |
| 4,965,047 A | 10/1990 | Hammond | | |
| 5,013,669 A * | 5/1991 | Peters, Jr. | G01N 33/54306 | 435/7.1 |
| 5,039,618 A * | 8/1991 | Stone | G01N 21/78 | 422/537 |
| 5,212,060 A * | 5/1993 | Maddox | B01L 3/5023 | 422/401 |
| 5,260,195 A * | 11/1993 | Azhar | C12N 11/08 | 422/400 |
| 5,278,075 A * | 1/1994 | Stone | G01N 33/84 | 422/412 |
| 5,296,380 A * | 3/1994 | Margalit | G01N 31/22 | 436/106 |
| 5,332,662 A * | 7/1994 | Ullman | C07D 219/06 | 435/188 |
| 5,334,502 A * | 8/1994 | Sangha | A61B 10/0051 | 422/412 |
| 5,457,054 A * | 10/1995 | Geisinger | G01N 33/946 | 422/413 |
| 5,523,051 A * | 6/1996 | Gibson | A01N 37/10 | 422/1 |
| 5,648,047 A | 7/1997 | Kardish et al. | | |
| 5,753,513 A * | 5/1998 | Amisar | G01N 33/946 | 436/901 |
| 5,858,797 A * | 1/1999 | Evtodienko | G01N 31/22 | 422/421 |
| 6,133,040 A * | 10/2000 | Glattstein | G01N 33/946 | 422/401 |
| 6,150,178 A * | 11/2000 | Cesarczyk | A61B 10/0045 | 422/412 |
| 6,420,181 B1 * | 7/2002 | Novak | G01N 31/22 | 210/658 |
| 6,514,769 B2 * | 2/2003 | Lee | B01L 3/5023 | 422/110 |
| 6,514,773 B1 * | 2/2003 | Klein | C07D 451/02 | 435/4 |
| 6,565,808 B2 * | 5/2003 | Hudak | B01L 3/5023 | 422/411 |
| 6,663,831 B2 * | 12/2003 | Konecke | A61B 10/0045 | 422/417 |
| 6,709,633 B2 * | 3/2004 | Etes | G01N 33/558 | 422/412 |
| 6,787,366 B1 * | 9/2004 | Novak | G01N 31/22 | 210/634 |
| 6,821,788 B2 * | 11/2004 | Cesarczyk | A61B 10/0045 | 422/412 |
| 7,114,403 B2 * | 10/2006 | Wu | A61B 10/0051 | 73/864.72 |
| 7,244,392 B1 * | 7/2007 | Konecke | A61B 10/007 | 422/408 |
| 7,319,032 B2 * | 1/2008 | Bohannon | G01N 33/54393 | 422/412 |
| 7,374,946 B2 * | 5/2008 | Glattstein | G01N 33/946 | 436/106 |
| 7,384,599 B2 * | 6/2008 | Brewer | G01N 31/22 | 422/417 |
| 7,455,813 B2 * | 11/2008 | Anderson | G01N 33/558 | 422/411 |
| 7,544,324 B2 * | 6/2009 | Tung | A61B 10/0045 | 422/504 |
| 7,879,293 B2 * | 2/2011 | Niedbala | A61B 10/0045 | 422/408 |
| 7,958,792 B2 * | 6/2011 | Peng | G01N 1/02 | 73/864.71 |
| 8,124,420 B2 * | 2/2012 | Amisar | G01N 31/22 | 210/634 |
| 8,647,451 B2 * | 2/2014 | Apblett | G01N 31/22 | 149/108.8 |
| 8,770,049 B2 * | 7/2014 | Pelssers | A61B 10/0045 | 422/411 |
| 9,759,733 B1 * | 9/2017 | Callahan | G01N 33/9486 | |
| 9,989,473 B2 * | 6/2018 | Callahan | G01N 21/78 | |
| 2001/0046710 A1 * | 11/2001 | Cutler | G01N 31/22 | 436/24 |
| 2002/0001854 A1 * | 1/2002 | Lee | B01L 3/5023 | 436/518 |
| 2002/0072124 A1 * | 6/2002 | Khan | G01N 33/54366 | 436/95 |
| 2002/0106809 A1 * | 8/2002 | Cesarczyk | A61B 10/0045 | 436/165 |
| 2002/0146346 A1 * | 10/2002 | Konecke | A61B 10/0045 | 422/417 |
| 2002/0173047 A1 * | 11/2002 | Hudak | B01L 3/5023 | 436/178 |
| 2003/0022392 A1 * | 1/2003 | Hudak | B01L 3/502 | 436/518 |
| 2003/0064526 A1 * | 4/2003 | Niedbala | A61B 10/0045 | 436/165 |
| 2004/0184954 A1 * | 9/2004 | Guo | A61B 10/0051 | 422/400 |
| 2004/0237674 A1 * | 12/2004 | Wu | A61B 10/0051 | 73/864 |
| 2005/0008538 A1 * | 1/2005 | Anderson | G01N 33/558 | 422/411 |
| 2005/0130312 A1 * | 6/2005 | Glattstein | G01N 33/946 | 436/93 |
| 2005/0277202 A1 * | 12/2005 | Fleming | G01N 33/558 | 436/514 |
| 2006/0286606 A1 * | 12/2006 | Oliver | B01L 9/54 | 435/7.1 |
| 2007/0128070 A1 * | 6/2007 | Wu | A61B 10/0051 | 422/400 |
| 2008/0044310 A1 * | 2/2008 | Haas | G01N 21/77 | 422/400 |
| 2008/0254550 A1 * | 10/2008 | Nathaniel | A61B 10/0045 | 436/165 |
| 2009/0004055 A1 * | 1/2009 | Darrigrand | A61B 10/0045 | 422/400 |
| 2009/0029480 A1 * | 1/2009 | Loane | G01N 21/78 | 436/170 |
| 2009/0068065 A1 * | 3/2009 | Pagoria | G01N 21/78 | 422/82.05 |
| 2010/0197516 A1 * | 8/2010 | Holmes | G01N 31/22 | 506/9 |
| 2011/0117664 A1 * | 5/2011 | Amisar | G01N 31/22 | 436/164 |
| 2011/0151570 A1 * | 6/2011 | Babichenko | G01N 33/52 | 436/93 |
| 2011/0239745 A1 * | 10/2011 | Satcher, Jr. | G01N 30/90 | 73/61.55 |
| 2012/0295362 A1 * | 11/2012 | Bland | G01N 33/946 | 436/92 |

(56) References Cited

U.S. PATENT DOCUMENTS

| | | | |
|---|---|---|---|
| 2013/0006068 A1* | 1/2013 | Gemer | A61B 10/0051 600/314 |
| 2013/0040289 A1* | 2/2013 | Jumonville | C12Q 1/28 435/5 |
| 2013/0157381 A1* | 6/2013 | Pang | G01N 33/5302 436/501 |
| 2014/0017802 A1* | 1/2014 | Smith | G01N 21/78 436/164 |
| 2014/0127824 A1* | 5/2014 | Amisar | G01N 21/78 436/107 |
| 2014/0134073 A1* | 5/2014 | Fuller | G01N 1/18 422/411 |
| 2015/0017732 A1* | 1/2015 | Wu | G01N 31/22 436/92 |
| 2015/0185125 A1* | 7/2015 | Danylewych-May | G01N 1/02 436/174 |
| 2015/0268215 A1* | 9/2015 | Tomellini | G01N 33/227 436/93 |
| 2016/0018424 A1* | 1/2016 | Lucas | G01N 33/52 436/93 |
| 2016/0077013 A1* | 3/2016 | Attar | G01N 31/22 422/402 |
| 2016/0109371 A1* | 4/2016 | Blair | G01N 21/645 436/172 |
| 2017/0082550 A1* | 3/2017 | Callahan | G01N 21/78 |

FOREIGN PATENT DOCUMENTS

| | | |
|---|---|---|
| AU | 2005100063 | 5/2005 |
| AU | 2005100064 | 5/2005 |
| AU | 2005100334 | 5/2005 |
| AU | 2005100335 | 5/2005 |
| AU | 2005100636 | 9/2005 |
| WO | 2006079167 A1 | 8/2006 |

OTHER PUBLICATIONS

Kidwell, D. A. et al, Forensic Science International 1997, 84, 75-86.*

Tsumura, Y. et al, Forensic Science International 2005, 155, 158-164.*

Haddoub, R. et al, New Journal of Chemistry 2011, 35, 1351-1354.*

Musile, G. et al, Analytical Methods 2015, 7, 8025-8033.*

* cited by examiner

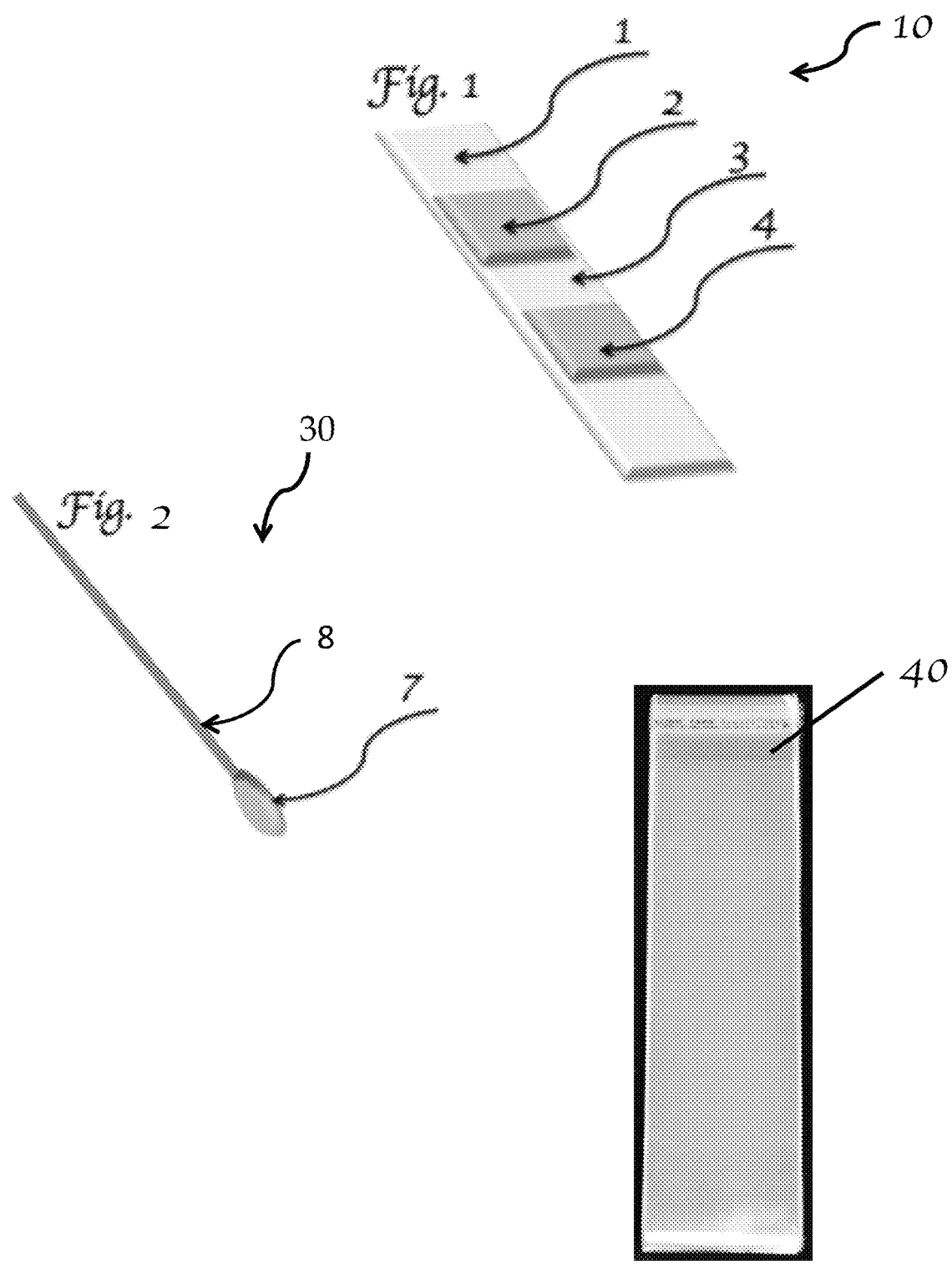

US 10,330,603 B1

MASS PRODUCED, LOW COST, PORTABLE TEST KIT FOR THE DETECTION AND IDENTIFICATION OF CHEMICAL AND BIOLOGICAL AGENTS

RELATED APPLICATION DATA

The present application is a continuation-in-part of commonly-owned U.S. application Ser. No. 15/094,825, entitled MASS PRODUCED, LOW COST, PORTABLE TEST KIT FOR THE DETECTION AND IDENTIFICATION OF NARCOTICS, filed on Apr. 8, 2016, now U.S. Pat. No. 9,759,733, which patent is related to commonly-owned U.S. application Ser. No. 14/856,671, entitled PORTABLE LIQUID ANALYZER, filed on Sep. 17, 2015, now U.S. Pat. No. 9,989,473. Both patents are incorporated herein by reference in their entireties.

TECHNICAL FIELD OF THE INVENTION

The present invention relates to a portable test kit capable of identifying the presence of chemical and biological agents, a process to inexpensively mass produce the portable test kit and achieve long term commercial shelf life in the range of 2 to 3 years, and a method to use the portable test kit.

BACKGROUND ART

Most commercially available presumptive chemical and biological agents test devices and available IP and literature, use and describe methods which contain hazardous materials and sophisticated packaging which are not suitable for extremely cheap mass production in simple factory settings.

These test kits suffer from a variety of manufacture and end use problems, including but not limited to: (i) kit construction requires liquid dropper bottles, breakable glass or plastic ampoules, blister packs and pressurized aerosol spray cans filled with hazardous liquid reagents; (ii) the presence of hazardous liquid reagents poses problems with manufacturing and exposure limitations, storage and handling, strict packaging requirements and significant shipping restrictions; (iii) the volume or quantity of liquid reagent consumed during one single test is excessive and wasteful adding to costly, bulky and often overly complicated device construction design and packaging; (iv) during use, operators may be exposed to sharps and hazardous liquid reagent splash or overspray; (v) most prior art devices require multi-step operations in order to complete a single test; and (vi) none of the prior art kits and devices achieve the bench mark of true low cost mass manufacturing, which would be considered in the range of tens of millions of individual units per annum, with a commercial shelf life span of 2 to 3 years.

Impregnation of bibulous carriers with reagent solutions is an incredibly inefficient and costly method of presumptive test kit manufacture. Ultimately, the solvents used to dissolve the powdered reagents must be removed by evaporation. Often the solvents will be aqueous based and acidic in nature, which makes removal from the bibulous carrier hazardous, very costly, and will require very sophisticated laboratory equipment to minimize exposure and corrosion of the surrounds. In the event that the bibulous carrier can be dried, it must still be cut and presented in a kit format for ease of use. Often, this will incorporate plastic injection molded housings, which are magnitudes of order more expensive than paper based supports. Additionally, the cost of the injection die is excessive. The alternative low cost paper based solid support carrier option for a presumptive kit is often not possible, as the loaded bibulous carrier strips resist sticking and adhering to common pressure sensitive adhesives because of interaction with the impregnated reagent(s) and/or the pressure sensitive adhesives react with the impregnated reagent(s), destroying the kits.

SUMMARY OF THE INVENTION

Embodiments of the present invention provide a presumptive spot test kit which will facilitate identification of chemical and biological agents within suspect residues.

Embodiments of the present invention provide a presumptive kit, constructed of paper with color change reagents applied to the surface as one or more test zones, and a pre-wetted swab with non-hazardous co-solvents to facilitate enhanced suspect residue collection.

Embodiments of the present invention provide an extremely portable presumptive test kit, which has true low cost and mass manufacture capability on the order of millions of units per annum, while achieving a commercial kit shelf life, on the order of several years, with a reduced false detection rate.

Embodiments of the present invention also provide a method of kit manufacture and use.

BRIEF DESCRIPTION OF THE DRAWINGS

FIG. 1 illustrates an embodiment of a diagnostic test paper made in accordance with the present invention;

FIG. 2 illustrates an embodiment of a swab made in accordance with the present invention; and FIG. 3 illustrates a package into which a test paper and swab may be hermetically sealed.

DETAILED DESCRIPTION OF THE PREFERRED EMBODIMENT

The described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention can be practiced without one or more of the specific details, or with other methods, components and so forth. In other instances, well-known structures, materials, or operations are not shown or described in detail to avoid obscuring aspects of the invention.

Chemical and Biological Agents are divided into several categories based on their mode of action on an organism.
  Blister agents:
    sulfur mustard (H, HD);
    nitrogen mustard (HN);
    lewisite (L);
    phosgene oxime (CX).
  Blood agents:
    hydrogen cyanide (AC)—Liquid, BP 26 deg cel. Volatile;
    cyanogen chloride (CK);
    arsine (SA). Lewisite (L) Adamsite.
  Nerve agents (nerve agents belong chemically to the group of organo-phosphorus compounds):
    Tabun, O-ethyl dimethylamidophosphorylcyanide (GA);
    Sarin, isopropyl methylphosphonofluoridate (GB);
    Soman, pinacolyl methylphosphonofluoridate (GD);

Cyclohexyl methylphosphonofluoridate (GF);
O-ethyl S-diisopropylaminomethyl methylphosphonothiolate (VX).
Psychotomimetic agents:
3-quinuclidinylbenzilate (BZ);
LSD.
Toxins:
Bacterial toxins;
Plant toxins.

Contrary to the prior approaches for the presumptive identification of chemical and biological agents, the inventor has discovered that presumptive polyvalent ion powdered salts, carbohydrates and polyols and color change reagents can be successfully mixed with and/or made into encapsulating polymer solutions and printed onto any solid support structure, to be shaped and packaged. In combination with a simple cotton swab, such as a Q-tip® swab, which has been pre-wetted with a non-hazardous solvent and packaged, Embodiments of the present invention provide a low cost, mass producible, portable test kit for the presumptive identification of chemical and biological agents.

FIG. 1 illustrates an embodiment of a diagnostic test paper 10 made in accordance with this invention. The test paper 10 comprises a solid support surface or article 1; one or more encapsulated colorimetric reagents (CR) 2, 4, printed at one or more locations onto the support surface 1; a physical gap or void 3 between the individual encapsulated reagent deposition interstices 2, 4 on the solid support surface 1 to prevent chemical interaction.

FIG. 2 illustrates an embodiment of a swab 30, such as a Q-tip® swab, made in accordance with the present invention. The swab 30 comprises a cotton tip matrix 7, dry or pre-wetted with one or more non-hazardous solvents, attached to one end of a handle 8.

Solid Support

Suitable solid support surfaces or substrates to which the encapsulated presumptive reagents can be applied, is dictated only by end use requirements. In accordance with the current invention and without limitation, in some embodiments the solid support substrate 1 is paper, such as 100-400 gsm white, acid free, card sheet.

Sample Swab

In order to maximize solubility of both the suspect residue of chemical and biological agents and the presumptive test reagents, a suitable non-hazardous solvent and/or solvent mix provided in combination with a swabbing device. Numerous swab and co-solvent devices can be prepared including, but not limited to, a pre-wetted cotton swab and/or co-solvent shaft filled pop or snap swabs.

In one embodiment a kit 10, the sample swab 30 is a pre-wetted, co-solvent, cotton swab 30. Numerous swab/solvent devices can be prepared including, but not limited to, dip impregnation, shaft-handle fill and pop or snap swabs. Pre-impregnation of swabs may be achieved in mass by fully automated dip or spray machinery.

The swab 30 may be a polypropylene handle 8 with a cotton filament matrix head 7. The sample swab may be dry or pre-impregnated with solvent to improve solubility of both CWA/BA and CR, maximizing sensitivity and color indication reactions. By way of example only, a suitable co-solvent is Iso-Propyl Alcohol ad-mixed with Dimethyl Sulphoxide. This co-solvent mix offers broad spectrum solubility of target and dry reagent compounds, while intensifying presumptive color change reactions. The combination of IPA with DMSO prevents freezing of solvents during long term storage and use in low temperature environments. This solvent combination also offers intensifying presumptive color change reactions, is non-hazardous, and has an extremely low cost. The volume of solvent required for pre-impregnation is in the range of 0.05-0.15 mL per swab.

Colorimetric Reagents

Colorimetric reagents (CR) may be selected according to at least: (a) liquid CR affinity for pre-adsorption onto dry, inert binders and subsequent milling into micronized powders; (b) powder CR affinity for milling into micronized powders; (c) degree of hygro-scopicity; (d) interaction with inert liquid diluents required for print manufacture; (e) level of UV and ambient condition degradation; and (f) selectivity for and color reaction intensity with CWA and BA.

Chemical Warfare Agent Detection

Without limitation, suitable CR capable of detecting gas and liquid phase pH changes may be selected from a group comprising: cresol red, methyl violet, crystal violet, ethyl violet, malachite green, methyl green, 2-(p-dimethylaminophenylazo)pyridine, paramethyl red, metanil yellow, 4-phenylazodiphenylamine, metacresol purple, orange IV, 4-o-tolylazo-o-toluidine, quinaldine red, 4,4'-bis(4-amino-1-naphthylazo)-2,2'-stilbenedisulfonic acid, p-naphtholbenzein, phenolphthalein, o-cresolphthalein, ethyl bis(2,4-dimethylphenyl)ethanoate, Thymolphthalein, alizarin yellow R, alizarin, p-(2,4-dihydroxyphenylazo) benzenesulfonic acid-sodium salt, 5,5'-indigodisulfonic acid-disodium salt, 2,4,6-trinitrotoluene, 1,3,5-trinitrobenzene, and clayton yellow.

Without limitation, suitable CR capable of detecting gas and liquid phase changes may be selected from a group comprising: merocyanine dyes, 4-[2-N-substituted-1,4-hydropyridin-4-ylidine)ethylidene]cyclohexa-2,5-di-en-1-one, red pyrazolone dyes, azomethine dyes, indoaniline dyes, diazamerocyanine dyes, indigoid dyes 2,6-diphenyl-4-(2,4,6-triphenylpyridinium-1-yl)phenolate, 1-ethyl-4-(methoxycarbonyl)pyridinium iodide,5-(dimethylamino)-5'-nitro-2,2'-bisthiophene, (2,4,6-triphenyl-I-pyridinio)-2,6-diphenylphenolate, and alizarin red s.

Without limitation, suitable CR capable of detecting the presence of liquid and solids comprising reactive nitrogen is determined by chemical reagents selected from a group comprising: 6-amino-1-naphthol-3-sulphonic acid, zinc, diphenylbenzidine, phenylanthranilic acid, aniline sulfate, diphenylamine, ethylenediamine, N-1 naphthyl dihydrochloride, potassium iodide, bismuth nitrate, and sodium hydrogen sulphate, hexachloroplatinic(IV) acid hydrate.

Without limitation, suitable CR capable of detecting the presence of volatile CWA (solid, liquid, gas) may be selected from a group comprising: sodium iodoplatinate, Alkyl magnesium bromide (Grignard reagent), B-napthol, selenious acid, indophenol blue, silver nitrate, Grignard's sodium iodide, sodium nitroprusside, quinone dichlorimide, mercuric nitrate, sodium iodide, N-chloramide, zinc Sulfate-Molybdic Acid, argentic nitrate, mercuric chloride, cuprous iodide, diphenylthiocarbazone, di-p-biphenylthiocarbazone, di-o-phenoxyphenylthiocarbazone, dianisylpropylene, p,p'-dinitrostilbene-o,o'-disodium sulfonate, 5-(or 8-) nitroisoquinoline, sodium iodoplatinate, chloroplatinic acid, phosphomolybdic acid, Mayer's reagent (KHgI2), metanil-yellow, N-chloramide, diphenylthiocarbazone, potassium iodide and starch, acidified phloxine, p-dimethylaminobenzaldehyde and syn-trimethoxybenzene, p-nitrobenzyl bromide, 4-(4-nitrobenzyl)pyridine-tetraethylenepentamine, palladium chloride, bromophthalein, anisaldehyde, 4-aminopyridine, 2-methylthioacridone, trichlorobenzoquinoneimide, zinc hexacyanoferrate, cupric acetate, malachite green, and p,p'-tetramethyldiaminodiphenylmethane (tetrabase).

Biological Agent Detection Without limitation, suitable CR capable of detecting BA may be selected from a group comprising: acid fuschin, alcian blue 8gx, alizarin red s, 9-amino-6-chloro-2-methoxyacridine, aniline blue, auramine o, azure b, N,N'-[1,2-ethanediylbis(oxy-2,1-phenylene)]bis[N-(carboxym-ethyl)-, benzothiazolium, 2,2'-[1,3 propanediylbis[(dimethyliminio)-3,1-propanediyl-1(4H)-pyridinyl-4-ylidenemethylidyne]]bis[3-methyl-, iodide (1:4), brilliant cresyl blue, calcein, congo red, crystal violet, di-8-anepps, dihydroethidium, dihydrorhodamine 123, eosin b, fast green fcf, bicinchoninic acid, sodium carbonate, sodium potassium tartrate, sodium hydroxide, copper sulphate, pyrogallol red, sodium molybdate, succinic acid, sodium benzoate sodium oxalate, methanol, coomassie blue G-250, ethanol, phosphoric acid, and phosphomolybdate, phosphotungstate.

Reagent and Encapsulating Polymer Mixing

In embodiments of the present invention, raw CR product may be individually micronized in suitable a agitation mill system such as a laboratory ball, crusher, shaker mill, or the like. The process produces a sub-micron size powder capable of undergoing laydown print applications.

The fine CR powder may be added to inert liquid diluents which double as solid support binding agents during the printing process. The two components may be combined in a high speed impeller mixer or shaker or similar system until an homogenized suspension is obtained. Without limitation, the liquid diluents may be selected from a list including but not limited to: acrylic acid, polyvinyl alcohol, amino cross-linking agents, polyvinyl pyrrolidone, glycol-ethers, styrene, polyester, vinyl chloride, polyethylene, natural gums, polyethers and polyamides. The viscosity of the homogenized CR suspension may be adjusted using inert bulking agents including but not limited to silica, diatomaceous earth and mixtures of liquid diluent and combinations thereof.

Reagent Deposition

Deposition of the powdered reagent(s) mixture onto the dry solid support may be achieved by any suitable large scale printing system using standard factory equipment. For example, letterpress, rotary gravure, screen printing, tampography, wax printing, contact dosing, ultrasonic sputter, and spray and drop on demand printing may be used. In one embodiment, the preferred printing system includes screen printing using fully automated roll to roll, 32-62 mesh, multi-layer, high durability, UV cured screens. The printing system further includes downstream drying, guillotining, vertical/horizontal form fill seal capability, with additional individual strip and pouch numbering.

Drying the CR coated solid support may be achieved by any large volume drying process including but not limited to: fan forced heated air, UV or IR cure.

During production, representative, live sample, in house, batch testing of printed sheet product. Quarterly, representative, live sample, in house, batch testing of printed strip product, through years 1, 2 and 3 post production.

As illustrated in FIG. 1, the individual dried encapsulated chemical reagents 2, 4 may be printed onto the solid support article 1 separated by a physical space 3 between the individual encapsulated reagent deposition interstices 2, 4, thus preventing chemical interaction and contamination of the reagents 2, 4 and maintain selectivity and reactivity for target molecule(s) and ion(s).

Packaging

In one embodiment of the present invention, the test kit, comprising both the sample collection swab 30 and a printed dry reagent test strip 10, may be packaged individually in separate, moisture and UV resistant packages 40 (FIG. 3) prior to use. Preferably the package 40 is a tear-open, form, fill, and seal sachet. The sachet 40 may be constructed from commercially available Paper/PET12 um/AL7 um/PE50 product, which is an extremely cheap, mass produced material. Individual pre-wetted sample swabs 30 and individual printed dry reagent test strips 10 be automatically packaged into individual sachets 40 by vertical and/or horizontal form fill seal machines.

Each test kit may include a test strip 10 printed with several CR 2, 4, thus achieving broad spectrum detection of CWA and BA. Kit manufacture may utilize various approaches, in order to prevent CR degradation and maintain long term (i.e. several years) CR viability. Without limitation, such approaches may include: direct printing of mixed CR suspension, where reaction between individual CR on a single test strip 10 does not occur; overlay printing of individual CR; individual CR suspensions printed with a physical separation or void 3 FIG. 1) between the boundary edge of one dried CR zone 2 and the next dried CR zone 4. The void 3 between dry CR zones 2, 4 on the solid support surface 1 may be a minimum of 1 mm. In addition, the printing of the CR suspension 2, 4 to the solid support 1 drying step occurs immediately post print. Finally, the shaped article is packaged within atmospheric, UV and moisture resistant packaging pouches 40.

Use of Kit

The kit (test strip 10 and swab 30, in the sealed package 40) may be carried in a pocket, belt case, glove box, brief case, etc. When a suspect residue or object is observed, both the sampling swab 30 and presumptive reagent strip 10 are removed from the sachet packaging 40. The swab 30 is rubbed into the suspect residue, liquid, gel, solid and/or across suitable surfaces for several seconds, to facilitate the collection of a representative sample of the suspect residue. The swab 30 with the collected sample is then rubbed through the colorimetric reagent test zones 2, 4 on the paper strip 1 for several seconds, facilitating a rapid yes/no positive/negative colorimetric indication on the test strip 1 or swab 30 for the presence of target chemical or biological agents.

BENEFITS

Embodiments of test kits the present invention provide numerous benefits over existing test methods. Among such benefits:

The test kits of the present invention replace the need for sample workup and preparation in a laboratory setting as required by TLC analysis and remove the hazardous liquified diazonium salt spray or other hazardous liquid reagents, with a miniature, highly portable, dry stabilized diazonium salt test strip. Sample preparation, laboratory equipment, and numerous sequential steps are not required to perform the test.

The test kits of the present invention replace all sophisticated laboratory procedures and equipment, with a single step diazonium salt encapsulation and paper strip laydown methodology. The test kits do not require breakable ampoule packaging, and prevent solvents like DMSO from freezing by the addition of non-hazardous, low cost co-solvent. Further, single test kits are designed for mass manufacture at low cost with a 2 to 3 year shelf life and have a greatly reduced false indication rate.

The description of the present invention has been presented for purposes of illustration and description, but is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A portable detection kit for identifying the presence of a target chemical or biological agent, comprising:
    a first homogenous suspension of a first dry chemical powder colorimetric reagent (CR) mixed with an inert liquid diluent, deposited and dried onto at least a first portion of a solid support article;
    a swab device pre-wetted with a solvent to facilitate the collection and transfer of a suspected chemical or biological agent residue to the coated solid support article and upon contacting the residue with the coated solid support article and mixing all components together on the coated solid support article, a known visual colorimetric indication is produced identifying a class of an unknown target chemical or biological agent present in the suspect residue; and
    a light, air, and moisture proof package into which the coated solid support article and the swab device are individual hermetically sealed prior to use.

2. The portable detection kit as in claim 1, wherein the first CR comprises a dry micronized powder which undergoes a characteristic color change when combined with a target chemical agent.

3. The portable detection kit as in claim 2, wherein the first CR is selected from the group consisting of: cresol red, methyl violet, crystal violet, ethyl violet, malachite green, methyl green, 2-(p-dimethylaminophenylazo)pyridine, paramethyl red, metanil yellow, 4-phenylazodiphenylamine, metacresol purple, orange IV, 4-o-tolylazo-o-toluidine, quinaldine red, 4,4'-bis(4-amino-1-naphthylazo)-2,2'-stilbenedisulfonic acid, p-naphtholbenzein, phenolphthalein, o-cresolphthalein, ethyl bis(2,4-dimethylphenyl)ethanoate, Thymolphthalein, alizarin yellow R, alizarin, p-(2,4-dihydroxyphenylazo) benzenesulfonic acid-sodium salt, 5,5'-indigodisulfonic acid-disodium salt, 2,4,6-trinitrotoluene, 1,3,5-trinitrobenzene, and clayton yellow.

4. The portable detection kit as in claim 2, wherein the first CR is selected from the group consisting of: merocyanine dyes, 4-[2-N-substituted-1,4-hydropyridin-4-ylidine) ethylidene]cyclohexa-2,5-di-en-1-one, red pyrazolone dyes, azomethine dyes, indoaniline dyes, diazamerocyanine dyes, indigoid dyes 2,6-diphenyl-4-(2,4,6-triphenylpyridinium-1-yl)phenolate, 1-ethyl-4-(methoxycarbonyl)pyridinium iodide,5-(dimethylamino)-5'-nitro-2,2'-bisthiophene, (2,4,6-triphenyl-I-pyridinio)-2,6-diphenylphenolate, alizarin red s.

5. The portable detection kit as in claim 4, wherein the first CR comprises a dry micronized powder which undergoes characteristic color change when combined with a target biological agent.

6. The portable detection kit as in claim 5, wherein the first CR is selected from the group consisting of: acid fuschin, alcian blue 8gx, alizarin red s, 9-amino-6-chloro-2-methoxyacridine, aniline blue, auramine o, azure b, N,N'-[1,2-ethanediylbis(oxy-2,1-phenylene)]bis[N-(carboxymethyl)-, benzothiazolium, 2,2'-[1,3 propanediylbis [(dimethyliminio)-3,1-propanediyl-1 (4H)-pyridinyl-4-ylidenemethylidyne]]bis[3-methyl-, iodide (1:4), brilliant cresyl blue, calcein, congo red, crystal violet, di-8-anepps, dihydroethidium, dihydrorhodamine 123, eosin b, fast green fcf, bicinchoninic acid, sodium carbonate, sodium potassium tartrate, sodium hydroxide, copper sulphate, pyrogallol red, sodium molybdate, succinic acid, sodium benzoate sodium oxalate, methanol, coomassie blue G-250, ethanol, phosphoric acid, and phosphomolybdate, phosphotungstate.

7. The portable detection kit as in claim 2, wherein the first CR is selected from the group consisting of: 6-amino-1-naphthol-3-sulphonic acid, zinc, diphenylbenzidine, phenylanthranilic acid, aniline sulfate, diphenylamine, ethylenediamine, N-1 naphthyl dihydrochloride, potassium iodide, bismuth nitrate, and sodium hydrogen sulphate, hexachloroplatinic(IV) acid hydrate.

8. The portable detection kit as in claim 2, wherein the first CR is selected from the group consisting of: sodium iodoplatinate, Alkyl magnesium bromide (Grignard reagent), B-napthol, selenious acid, indophenol blue, silver nitrate, Grignard's sodium iodide, sodium nitroprusside, quinone dichlorimide, mercuric nitrate, sodium iodide, N-chloramide, zinc Sulfate-Molybdic Acid, argentic nitrate, mercuric chloride, cuprous iodide, diphenylthiocarbazone, di-p-biphenylthiocarbazone, di-o-phenoxyphenylthiocarbazone, dianisylpropylene, p,p'-dinitrostilbene-o,o'-disodium sulfonate, 5-(or 8-) nitroisoquinoline, sodium iodoplatinate, chloroplatinic acid, phosphomolybdic acid, Mayer's reagent (KHgI2), metanil-yellow, N-chloramide, diphenylthiocarbazone, potassium iodide and starch, acidified phloxine, p-dimethylaminobenzaldehyde and syn-trimethoxybenzene, p-nitrobenzyl bromide, 4-(4-nitrobenzyl)pyridine-tetraethylenepentamine, palladium chloride, bromophthalein, anisaldehyde, 4-aminopyridine, 2-methylthioacridone, trichlorobenzoquinoneimide, zinc hexacyanoferrate, cupric acetate, malachite green, and p,p'-tetramethyldiaminodiphenylmethane (tetrabase).

9. The portable detection kit as in claim 1, wherein the inert liquid diluent is selected from the group consisting of acrylic acid, polyvinyl alcohol, amino cross-linking agents, polyvinyl pyrrolidone, glycol-ethers, styrene, polyester, vinyl chloride, polyethylene, natural gums, poly-ethers, and polyamides.

10. The portable detection kit as in claim 1, wherein the first homogeneous suspension further comprises an inert bulking agent.

11. The portable detection kit as in claim 1, wherein the swab device comprises:
    a handle; and
    an absorbent matrix collection tip for surface sample collection and physical mixing of the suspect residue and the first homogenous suspension.

12. The portable detection kit as in claim 11, wherein the inert bulking agent is selected from the group consisting of silica, diatomaceous earth, mixtures of liquid diluent, and combinations thereof.

13. The portable detection kit as in claim 1, further comprising a second homogenous suspension of a second CR deposited and dried onto a second portion of the solid support item separated from the first portion.

14. The portable detection kit as in claim 1, wherein the coated solid support article is formed into a strip.

15. The portable detection kit as in claim 1, wherein the solid support article is selected from the group consisting of glass, metal, paper, textiles, organic membranes, inorganic membranes, natural fibers, and synthetic fibers.

16. The portable detection kit as in claim 11, wherein the swab tip comprises a dry tip.

17. The portable detection kit as in claim 11, wherein the swab tip comprises a tip pre-wetted with a solvent.

18. The portable detection kit as in claim 17, wherein the pre-wetted solvent comprises an aqueous solvent or an organic solvent.

19. The portable detection kit as in claim 18, wherein the organic solvent is selected from the group consisting of alcohols, acetone, chlorinated hydrocarbons, dimethyl sulfoxide, and organic acids.

20. The portable detection kit as in claim 18, wherein the aqueous solvent is selected from the group consisting of water, mineral acids and alkali.

21. The portable detection kit as in claim 1, wherein the package comprises a layer of a PET or cellulosic material, a layer of aluminum, and a layer of a Poly Ethylene material.

22. The portable detection kit as in claim 21, wherein:
the layer of a PET or cellulosic material is approximately 12 microns thick;
the layer of aluminum is approximately 7 microns thick; and
the layer of a Poly Ethylene material is approximately 50 microns thick.

23. A method of providing a portable detection kit for identifying the presence of a target chemical or biological agent, comprising:
mixing a homogenous suspension of a dry chemical powder colorimetric reagent (CR) with an inert liquid diluent;
depositing the homogeneous suspension onto a solid support article;
drying the homogeneous suspension to coat the solid support article;
pre-wetting a swab device with a solvent to facilitate the collection and transfer of a suspected chemical or biological agent residue to the coated solid support article and upon contacting the residue with the coated solid support article and mixing all components together on the solid support article, a known visual colorimetric indication is produced thereby identifying a class of an unknown target chemical or biological agent present in the suspect residue; and
hermetically sealing the coated solid support article and the swab device in a light, air, and moisture proof package prior to use.

24. The method as in claim 23, further comprising processing the CR in a ball, crusher, or shaker mill to produce a sub-micron mesh size powder.

25. The method as in claim 24, further comprising mixing the CR with an inert liquid diluent in mixing containers and high speed shaker beds or in rotary impeller mixers.

26. The method as in claim 23, wherein depositing the homogenous suspension onto the solid support article comprises an automated commercial printing process.

27. The method as in claim 23, wherein the commercial printing process is selected from the group consisting of letterpress, rotary gravure, screen printing, tampography, wax printing, contact dosing, ultrasonic sputter, and drop on demand printing.

28. The method as in claim 23, wherein drying the deposited homogenous suspension comprises a process selected from the group consisting of UV, IR, and hot air cure.

29. The method as in claim 23, further comprising forming the coated solid support article into a predetermined shape by a process selected from the group consisting of injection molding, pressure forming, guillotining, and die-cutting.

30. The method as in claim 23, wherein depositing the homogenous suspension comprises depositing a plurality of homogenous suspensions, each comprising a different CR, onto the solid support article, the plurality of homogenous suspensions separated by physical voids therebetween.

31. The method as in claim 23, further comprising hermetically sealing the coated solid support article and the swab device in the package by vertical or horizontal form fill seal packaging systems.

32. The method according to claim 23, further comprising testing for the presence of a target chemical or biological agent by:
removing the coated solid support and swab device from the sealed package;
rubbing an object with the swab device to transfer a molecule or ion of an unknown suspect residue from the object to the swab device;
contacting the swab device with the homogenous suspension on the solid support article to transfer the molecule or ion to the homogenous suspension; and
rubbing the swab device through the homogenous suspension on the solid support article to mix together the suspect residue, the homogenous suspension, and the swab wetting solvent;
whereby a chemical reaction is facilitated to produce a presumptive colorimetric indication of the presence of a target chemical or biological agent if a target chemical or biological agent is present.

* * * * *